US009851357B2

(12) United States Patent
Sautes-Fridman et al.

(10) Patent No.: US 9,851,357 B2
(45) Date of Patent: Dec. 26, 2017

(54) METHOD FOR THE PROGNOSIS OF SURVIVAL TIME OF A PATIENT SUFFERING FROM A SOLID CANCER

(71) Applicants: INSERM (INSTITUT NATIONAL DE LA SANTÉ ET DE LA RECHERCHE MÉDICALE), Paris (FR); UNIVERSITE PARIS DESCARTES, Paris (FR); UNIVERSITE PIERRE ET MARIE CURIE (PARIS 6), Paris (FR); ASSISTANCE PUBLIQUE HOPITAUX DE PARIS, Paris (FR)

(72) Inventors: Catherine Sautes-Fridman, Paris (FR); Wolf-Herve Fridman, Paris (FR); Marie-Caroline Dieu-Nosjean, Paris (FR); Jeremy Goc, Paris (FR)

(73) Assignees: INSERM (INSTITUTE NATIONAL DE LA SANTE ET DE LA RECHERCHE MEDICALE, Paris (FR); UNIVERSITE PARIS DESCARTES, Paris (FR); UNIVERSITE PIERRE ET MARIE CURIE (PARIS6), Paris (FR); ASSISTANCE PUBLIQUE HOPITAUX DE PARIS, Paris (FR)

( * ) Notice: Subject to any disclaimer, the term of this patent is extended or adjusted under 35 U.S.C. 154(b) by 0 days.

(21) Appl. No.: 14/905,177

(22) PCT Filed: Jul. 11, 2014

(86) PCT No.: PCT/EP2014/064886
§ 371 (c)(1),
(2) Date: Jan. 14, 2016

(87) PCT Pub. No.: WO2015/007625
PCT Pub. Date: Jan. 22, 2015

(65) Prior Publication Data
US 2016/0146820 A1 May 26, 2016

(30) Foreign Application Priority Data
Jul. 15, 2013 (EP) .................................... 13306004

(51) Int. Cl.
G01N 31/00 (2006.01)
G01N 33/53 (2006.01)
G01N 33/574 (2006.01)
G01N 33/569 (2006.01)

(52) U.S. Cl.
CPC . *G01N 33/57423* (2013.01); *G01N 33/56966* (2013.01); *G01N 2333/70517* (2013.01); *G01N 2333/70596* (2013.01); *G01N 2800/52* (2013.01); *G01N 2800/54* (2013.01)

(58) Field of Classification Search
CPC ..... C07K 14/435; C12N 15/11; C12N 15/111; C12N 2310/14; C12N 2320/30
See application file for complete search history.

(56) References Cited

U.S. PATENT DOCUMENTS 6,228,540 B1 * 5/2001 Kobayashi ................ G03F 1/68
430/330
2009/0215053 A1 * 8/2009 Galon .............. G01N 33/57484
435/6.16

OTHER PUBLICATIONS

Dieu-Nosjean et al. ("Dieu", J. Clin. Onco., 2008, 26, 4410-441).*
Dieu-Nosjean et al. (Journal of Clinical Oncology, vol. 26, No. 27, Sep. 20, 2008, pp. 4410-4417).*
Ladanyi et al ("Ladanyi", 2011, Cancer Immunol. Immunother. 60, 1729-1738).*
Remark et al., "Characteristics and Clinical Impacts of the Immune Environments in Colorectal and Renal Cell Carcinoma Lung Metastases: Influence of Tumor Origin", Clinical Cancer Research, Jun. 19, 2013, vol. 19, No. 15, p. 4079-4091.
Pages et al., "Immune Infiltration in Human Tumors: a Prognostic Factor that Should not be Ignored", Oncogene, Feb. 23, 2010, vol. 29, No. 8, p. 1093-1102.
Kawai et al., "Predominant Infiltration of Macrophages and CD8 + T Cells in Cancer Nests is a Significant Predictor of Survival in Stage IV Nonsmall Cell Lung Cancer", Cancer, Sep. 15, 2008, vol. 113, No. 6, p. 1387-1395.
Hiraoka et al., "Concurrent Infiltration by CD8 + T Cells and CD4 + T Cells is a Favourable Prognostic Factor in Non-Small- Cell Lung Carcinoma" British Journal of Cancer, Jan. 30, 2006, vol. 94, No. 2, p. 275-280.

* cited by examiner

*Primary Examiner* — Lisa Cook
(74) *Attorney, Agent, or Firm* — Whitham, Curtis & Cook

(57) ABSTRACT

The present invention relates to an in vitro method for the prognosis of survival of a patient suffering from a solid cancer, comprising the quantification of the cell density of CD8+ cells and DC-LAMP+ dendritic cells present in a tumor tissue sample from said patient, wherein a high density of CD8+ cells and DC-LAMP+ dendritic cells indicates that the patient has a favorable prognosis, a high density of CD8+ cells and a low density of DC-LAMP+ dendritic cells indicates that the patient has a poor prognosis, and a low density of CD8+ cells and DC-LAMP+ dendritic cells indicates that the patient has the worst prognosis.

16 Claims, 5 Drawing Sheets

Figure 1:
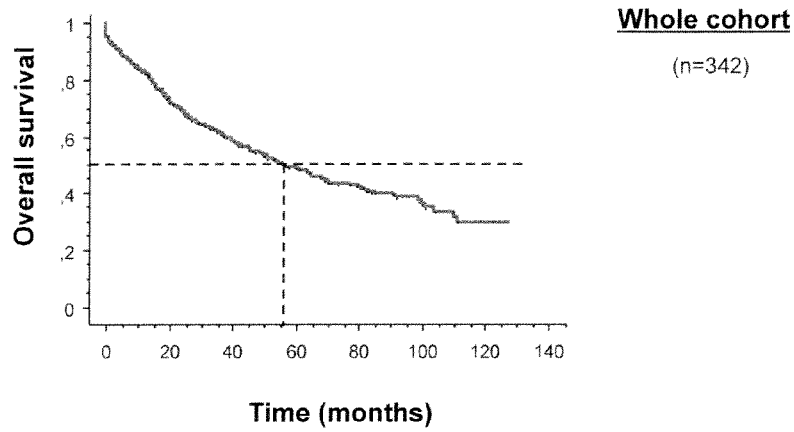
Figure 1:
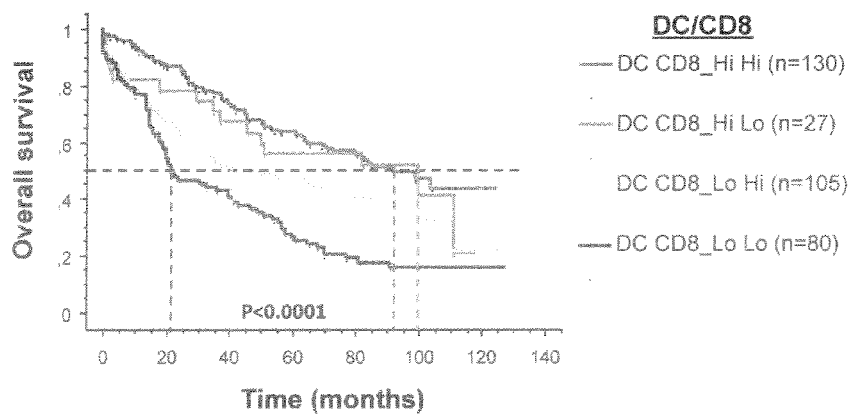

| Time (months) | 0 | 20 | 40 | 60 | 80 | 100 | 120 |
|---|---|---|---|---|---|---|---|
| at risk | 323 | 245 | 197 | 161 | 128 | 28 | 6 |
| events | 18 | 96 | 143 | 175 | 197 | 207 | 211 |
| censored | 1 | 1 | 2 | 6 | 17 | 107 | 125 |

METHOD FOR THE PROGNOSIS OF SURVIVAL TIME OF A PATIENT SUFFERING FROM A SOLID CANCER

FIELD OF THE INVENTION

The present invention relates to an in vitro method for the prognosis of survival time of a patient suffering from a solid cancer.

BACKGROUND OF THE INVENTION

As indicated in Dieu-Nosjean et al. (J Clin Oncol 26:4410-4417. 2008), lung cancer is the most common cause of cancer related death in the world. Approximately 80% to 90% of cases involve Non-Small-Cell Lung Cancer (NSCLC), which includes adenocarcinoma and squamous cell carcinoma. Only patients whose tumors can be completely resected have a significant chance of increased survival. However, as many as 30% of patients with stage I disease experience recurrence after surgery. The correlation between tumor-infiltrating immune cells and the prognosis of patients with lung cancer is controversial.

A tumor is composed of malignant, stromal, endothelial, and immune cells that form a heterogeneous network and exhibit complex interactions. Although tumor eradication by the immune system is often inefficient, there is evidence that many developing cancers are not ignored by the immune system. Spontaneous tumor regressions occurring concomitantly with autoimmune manifestations and the higher incidence of tumors in immunosuppressed patients are indications of the involvement of the immune system in tumor rejection. Mice deficient in immune functions spontaneously develop tumors. The density of tumor-infiltrating lymphocytes (TILs) with cytotoxic and memory phenotypes is highly predictive of good clinical outcome in many solid tumors. However, although prognosis is related to the homing of effector immune cells, it is still unclear where the activation of the specific immune response takes place: in the tumor, the draining lymph node, or both.

It is now well established that immune responses can take place at distance of secondary lymphoid organs, in tertiary lymphoid structures (TLS). Dieu-Nosjean et al. have observed that these lymph node-like structures can develop in lung cancer patients. They have been named "Tumor-induced Bronchus-Associated Lymphoid Tissues" (Ti-BALT) as they were never found in the non-tumoral tissues of NSCLC patients. Moreover, Dieu-Nosjean et al. have demonstrated that the density of mature DC, a population which was selectively detected in Ti-BALT, is associated with a favorable clinical outcome in patients with early-stage NSCLC (Dieu-Nosjean et al., J. Clin. Oncol., 2008), and in metastatic stage (Remark et al., Clin Cancer Res. 2013 Jun. 19), suggesting that they represent an activation site for tumor-specific T cells.

The presence of TLS has been reported in other human tumors e.g. colorectal cancer (Coppola et al., Am J Pathol., 2011; 179(1):37-45; McMullen et al., Clin Exp Immunol. 2010; 161(1):81-8;), breast cancer (Gobert et al., Cancer Res 2009; 69(5) 2000-2009; Martinet et al., Cancer Res. 2011; 71(17) 5678-87; Gu-Trantien et al., J Clin Invest. 2013; 123(7):2873-92) and melanoma (Martinet et al., Cancer Res. 2011; 71(17) 5678-87; Cipponi et al., Cancer Res. 2012; 72(16):3997-4007) indicating that ectopic lymphoid structures arise in many solid tumors.

SUMMARY OF THE INVENTION

The present invention relates to an in vitro method for the prognosis of survival of a patient suffering from a solid cancer, comprising the quantification of the cell density of CD8+ cells and DC-LAMP+ dendritic cells present in a tumor tissue sample from said patient, wherein a high density of CD8+ cells and DC-LAMP+ dendritic cells indicates that the patient has a favorable prognosis, a high density of CD8+ cells and a low density of DC-LAMP+ dendritic cells indicates that the patient has a poor prognosis, and a low density of CD8+ cells and DC-LAMP+ dendritic cells indicates that the patient has the worst prognosis.

The method fulfils a long-felt and ongoing need in the art to correctly and accurately predict the likely course or outcome of cancer in a patient, as reflected in survival time. The ability to do so enables medical practitioners to individually adapt cancer treatment protocols to particular patients. Patients who, according to the present method, have a high probability of a good therapy outcome may not need to receive the most aggressive treatments in order to experience a favorable outcome, and thus can avoid or minimize the side effects associated with such treatments, whereas patients with a poor prognosis can be treated aggressively at the earliest possible stage of the disease or by another therapy than the one used.

Furthermore, the combination of the method of the invention and the UICC-TNM classification, which is the currently used staging method lead to a method for the prognosis of survival with even higher accuracy.

DETAILED DESCRIPTION OF THE INVENTION

The present invention relates to an in vitro method for the prognosis of survival of a patient suffering from a solid cancer, comprising the following steps:
  a) quantifying, in a tumor tissue sample from said patient, the cell density of CD8+ cells,
  b) quantifying, in a tumor-induced lymphoid structure from said patient, the cell density of DC-LAMP+ dendritic cells,
  c) comparing cell density values obtained at step a) and b) with predetermined reference values for each type of cells at each location, and
  d) providing a favorable prognosis of survival time for said patient when the cell density of CD8+ cells and DC-LAMP+ dendritic cells are higher than said predetermined reference values,
     providing a poor prognosis of survival time for said patient when the cell density of CD8+ cells and DC-LAMP+ dendritic cells are lower than said predetermined reference values, or
     providing an intermediate prognosis of survival time for said patient when the cell density of one marker is higher than said predetermined reference value and the cell density of the other marker is lower than said predetermined reference value.

The method of prognosis according to the invention may be used alone or in combination with any other methods already used for the prognostic assessment of solid cancers, including but not limiting to stage, demographic and anthropometric parameters, results of routine clinical or laboratory examination, including size of the tumor, presence or absence of tumoral emboli, and presence or absence of lymph node invasion.

By tumor-induced lymphoid structure, it is meant the organization of tumor-infiltrating leukocytes into lymph-node like structure (also called Tertiary lymphoid structures) in the stroma of the tumor mass and, is composed of mature dendritic cell-T cell clusters (T-cell areas) and B-cell follicles (B-cell areas). Typically, depending on the tumor section, only one out of the two areas or both areas can be observed. This organization was called Ti-BALT for Tumor-induced Bronchus-Associated Lymphoid Tissues in lung cancer.

By mature dendritic cells, it is meant a population of dendritic cells that are professional for the presentation of processed antigens to T cells. Mature dendritic cells infiltrating the tumor are selectively located in contact with T cells, in the T-cell rich areas of the tumor-induced lymphoid structure.

In a preferred embodiment, the method of the invention is used in combination with TNM staging classification of the tumor (UICC-TNM classification, 2009), as the combination of DC-LAMP+ DCs, CD8+ cells and the tumor stage constitutes an even more powerful prognostic method for overall survival.

In an embodiment of the invention, the patient is a patient with a tumor of small size, i.e. the pathological T stage of the cancer of the patient is pT1.

In an alternative embodiment, the patient is a patient with a tumor of intermediate size, i.e. the pathological T stage of the cancer of the patient is pT2.

In yet another embodiment, the patient is a patient with a tumor of larger size, i.e. the pathological T stage of the cancer of the patient is pT3 or pT4.

In another embodiment, the cancer did not spread to nearby lymph nodes, i.e. the pathological N stage of the cancer of the patient is pN0.

In yet another embodiment, the cancer did spread to nearby lymph nodes, i.e. the pathological N stage of the cancer of the patient is pN1 or pN2.

In another embodiment, the tumor of the patient metastasized, the pathological M stage of the cancer is pM1.

In another embodiment, the tumor of the patient did not metastasize, the pathological M stage of the cancer is pM0.

In another embodiment, the patient is a patient with an early-stage of cancer, such as stage I cancer.

In yet another embodiment, the patient is a patient with a stage II cancer.

In yet another embodiment, the patient is a patient with an advanced-stage of cancer, such as a stage III cancer.

In an embodiment of the invention, the patient is a patient with early-stage of cancer who did not receive any neo-adjuvant, nor adjuvant therapy, such as chemotherapy and/or radiotherapy.

In an alternative embodiment of the invention, the patient is a patient with advanced-stage of cancer who receives adjuvant therapy with or without neo-adjuvant therapy, such as chemotherapy and/or radiotherapy.

The stages of multiple cancers are defined for example in UICC. TNM Classification of Malignant Tumours. 7th ed. Sobin L H, Gospodarowicz M, Wittekind Ch: New York, 2009.

Typically the tumor tissue sample is selected from the group consisting of (i) a global primary tumor sample (as a whole), (ii) a tumor nest sample, (iii) a stroma sample of the whole tumor section and (iv) a tumor-induced lymphoid structure sample.

Cells nests are small focus or accumulation of one type of cell that is different from the other cells in the tissue. Hence, tumor nests are an accumulation of tumor cells surrounded by non-cancerous cells.

The stroma is the connective, supportive framework of a biological cell, tissue or organ. In tumors, stroma cells are non-tumor cells. It comprises connective tissue, vessels, leukocytes and extracellular matrix.

In a more preferred embodiment, CD8+ cells are quantified in a stroma sample of the whole tumor section.

The survival defined in the method of the invention can be the overall survival (OS), the disease-free survival (DFS) or the disease-specific survival (DSS). In a preferred embodiment, the survival is the overall survival (OS).

Examples of solid cancers with tumor-induced lymphoid structures are lung cancers, colorectal cancers and breast cancers.

In a preferred embodiment, the solid cancer is a lung cancer.

In a more preferred embodiment, the solid cancer is a non-small cell lung cancer.

Typically CD8+ cells density and the DC-LAMP+ dendritic cells density may be measured for example by immunohistochemistry performed on a tumor sections (frozen or paraffin-embedded tissue sections) of sample obtained by biopsy.

In an embodiment of the method of the invention, CD8+ cells are enumerated in the tumor nests and the stroma of the whole tumor section with Calopix software (Tribvn), and expressed as an absolute number of positive cells/$\mu m^2$ of the surface area of the tumor, with SEMs calculated.

In an embodiment of the invention, DC-LAMP+ dendritic cells are detected by immunohistochemistry with an antibody against the DC-LAMP (CD208) molecule. Mature dendritic cells are counted on the whole tumor section. The density of cells may be expressed as the number of cells that are counted per one unit of surface area of the tumor section, e.g. as the number of cells that are counted per intermediate-power field (original magnification ×100) or $\mu m^2$ of the surface area of the tumor.

Typically, the predetermined reference values for the cell density of CD8+ cells and for the cell density of dendritic cells may be determined by applying statistical methods in large-scale studies on cancer patients.

An embodiment of the invention relates to a method for treating by adjuvant therapy a patient suffering from a solid cancer, wherein said method comprises the following steps:
 a) identifying a patient with a poor prognosis of survival with a method of prognosis of the invention, and
 b) treating with adjuvant therapy the patient identified.

The invention also relates to an anticancerous compound for use in a method for treating by adjuvant therapy a patient suffering from a solid cancer, wherein said method comprises the following steps:
 a) identifying a patient with a poor prognosis of survival with a method of prognosis of the invention, and
 b) treating with the anticancerous compound the patient identified.

Typically, anticancerous compounds are a cytotoxic agent, either a cytotoxic drug or a cytotoxic radioisotope. Examples of cytotoxic drugs are, without limitation, platinum salts, taxanes, vinca derivatives and analogues, gemcitabine, methotrexate, doxorubicin, cytotoxin such as *Pseudomonas* exotoxin, g protein, and g protein-coupled receptor inhibitors. Common cytotoxic radioisotopes are, for example, $^{131}I$, $^{90}Y$, $^{77}Lu$, $^{67}Cu$, $^{186}Re$, $^{188}Re$, $^{212}Bi$ and $^{213}Bi$.

In the following, the invention will be illustrated by means of the following examples and figures.

FIGURES

FIG. 1: Overall survival for the whole cohort of NSCLC patients as well as for patients stratified by DC and CD8+ cell density Kaplan-Meier curves of overall survival for 342 NSCLC patients: (A) whole patients, and (B) patients depending on DC/CD8 score. Differences between groups of patients were evaluated using the log-rank test. Log-rank P values were corrected using the formula proposed by Altman et al. (Altman D G, Lausen B, Sauerbrei W, Schumacher M. Dangers of using "optimal" cutpoints in the evaluation of prognostic factors. Medical Statistics Laboratory, Imperial Cancer Research Fund, London, England. J Natl Cancer Inst. 1994 Jun. 1; 86(11):829-35.)

Figure 2:
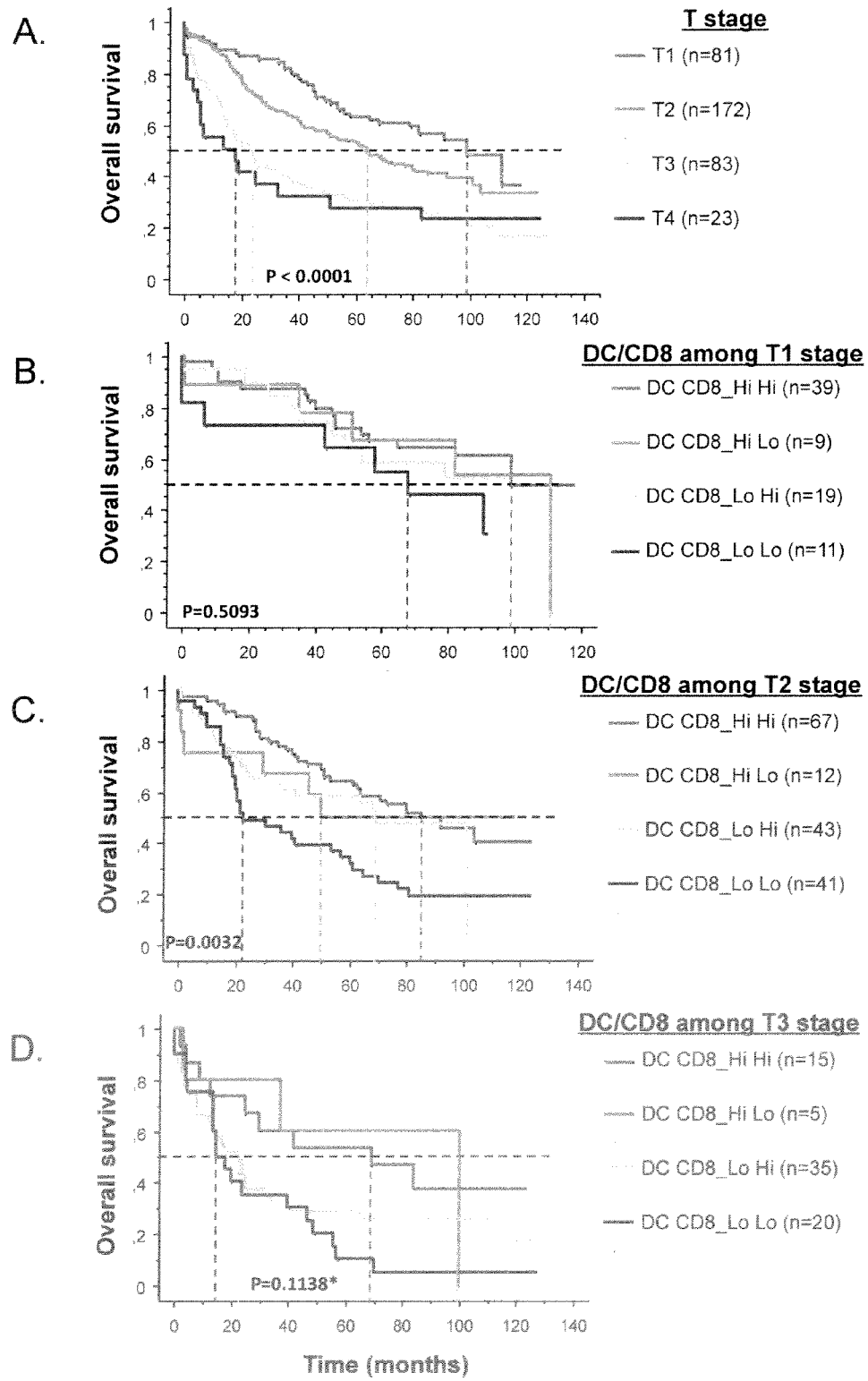

FIG. 2: Overall survival for NSCLC patients according to T stage and DC/CD8 score per T stage Kaplan-Meier curves of overall survival for 359 NSCLC patients depending on the pathologic T stage (A), and DC/CD8 score among T1 (B), T2 (C), and T3 (D) stages. Differences between groups of patients were evaluated using the log-rank test. Log-rank P values were corrected using the formula proposed by Altman et al.

Figure 3:
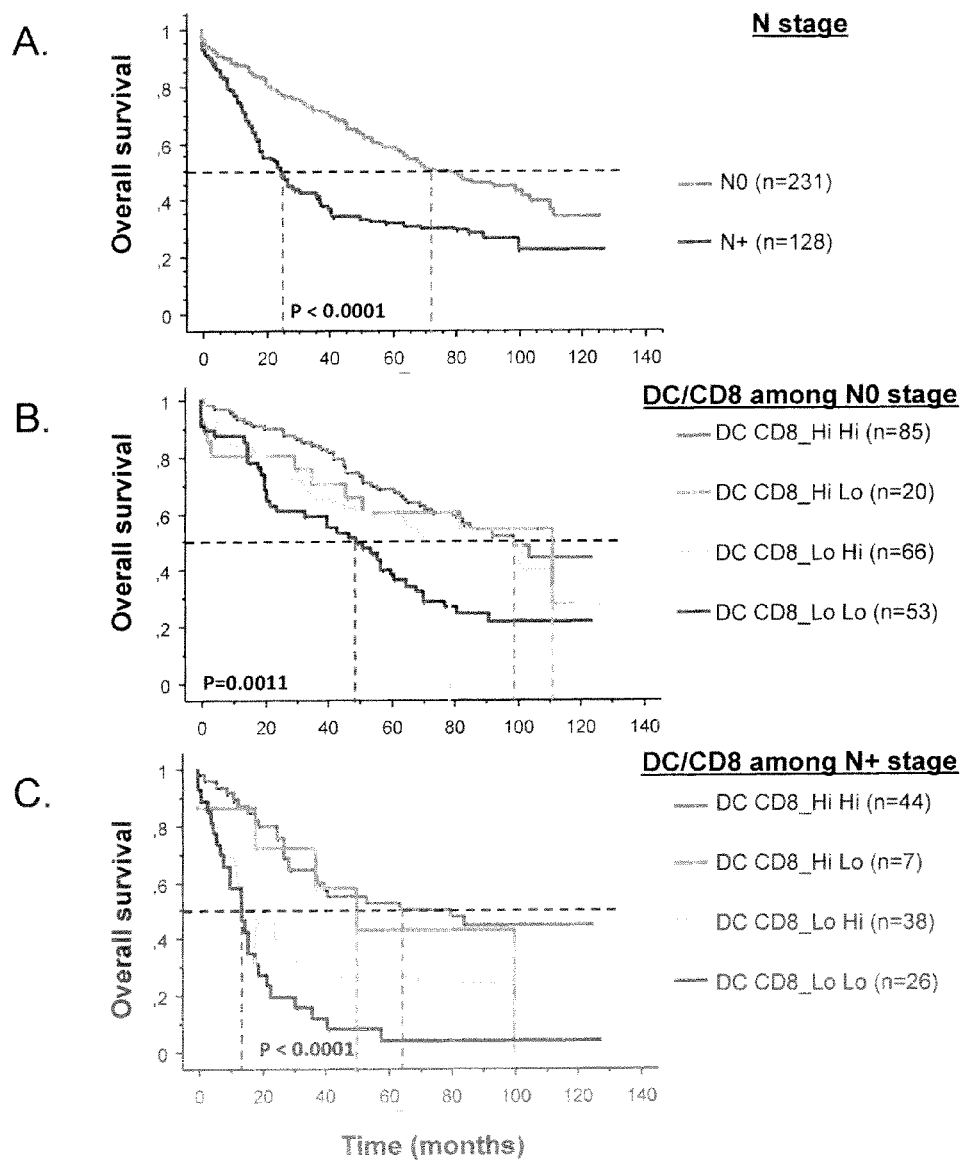

FIG. 3: Overall survival for NSCLC patients according to N stage and DC/CD8 score per N stage Kaplan-Meier curves of overall survival for 359 NSCLC patients depending on the pathologic N stage (A), and DC/CD8 score among N0 (B) and N positive (C) stages. Differences between groups of patients were evaluated using the log-rank test. Log-rank P values were corrected using the formula proposed by Altman et al.

Figure 4:
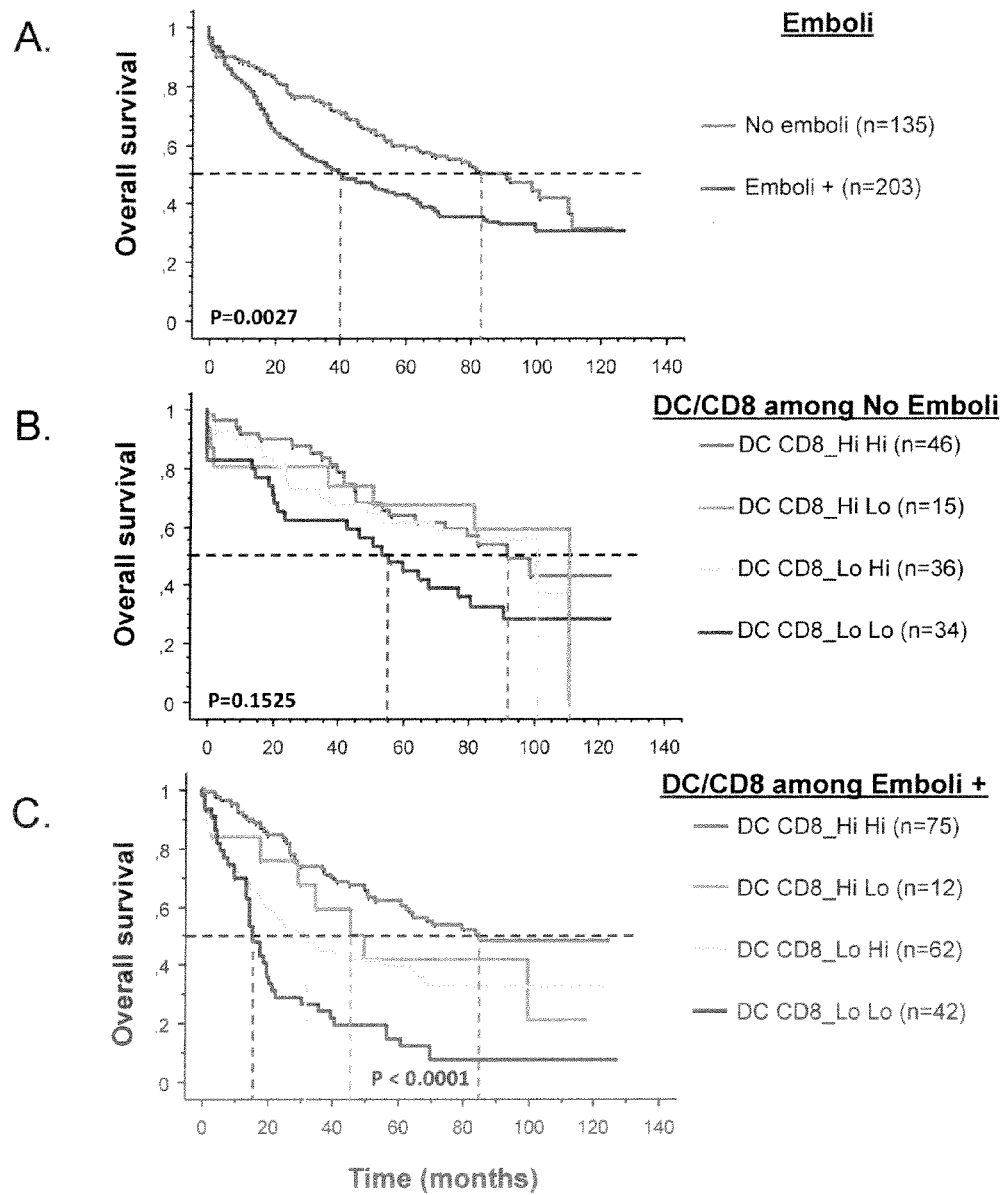

FIG. 4: Overall survival for NSCLC patients according to emboli and DC/CD8 score with or without emboli Kaplan-Meier curves of overall survival for 338 NSCLC patients depending on the emboli (A), and DC/CD8 score among patients without (B) or with emboli (C). Differences between groups of patients were evaluated using the log-rank test. Log-rank P values were corrected using the formula proposed by Altman et al.

Figure 5:
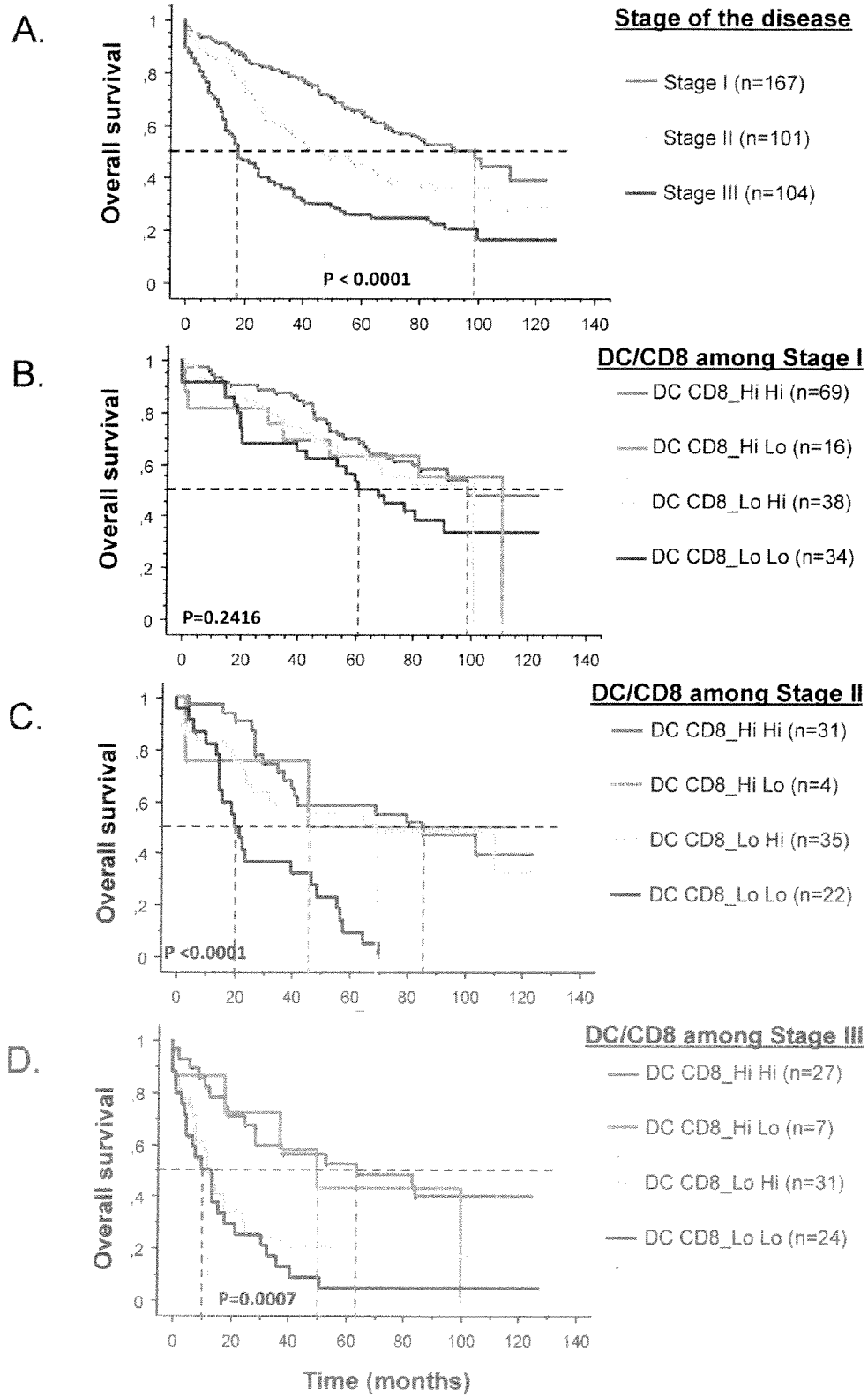

FIG. 5: Overall survival for NSCLC patients according to pTNM stage and DC/CD8 score per pTNM stage Kaplan-Meier curves of overall survival for 372 NSCLC patients depending on the pathologic TNM stage (A), and DC/CD8 score among stage I (B), stage II (C), and stage III (D). Differences between groups of patients were evaluated using the log-rank test. Log-rank P values were corrected using the formula proposed by Altman et al.

EXAMPLES

Example 1

Patients

Fresh (n=54 patients), frozen (n=28 patients), and paraffin-embedded (n=376 patients) lung tumor samples were obtained from NSCLC patients who underwent a complete surgical resection of their lung tumors at Institut Mutualiste Montsouris or Hotel Dieu Hospital (Paris, France). 376 NSCLC patients (stages I to IV, UICC TNM classification 2009) operated between Jun. 15, 2001 and Nov. 26, 2004 were retrieved retrospectively. The classification of the tumor grade was made following the recommendation of the 7$^{th}$ edition of the TNM classification of malignant tumors published by the International Union Against Cancer and the American Joint Committee on Cancer (Sobin, Cancer, 2010). Patients who received neo-adjuvant chemotherapy or radiotherapy were ineligible. The observation time of the cohort was the interval between the surgery and the last contact (last follow-up or death of the patient). At the completion of the study, the minimal clinical follow-up was 90 months for the last patient included in the cohort. The data on long-term outcomes were obtained retrospectively by interrogation of municipality registers or the family of patients. A written informed consent was obtained from the patients prior to inclusion in the prospective study. The protocol was approved by the local ethics committee (n°: 2008-133 and 2012-0612) in application with the article L.1121-1 of French law.

Flow Cytometry

Fresh lung tumor specimens were mechanically dissociated and mononuclear cells were isolated as previously described (De Chaisemartin, L. et al. *Cancer Res* 71, 6391-6399 (2011)). Mononuclear cells were stained with multiple panels of antibodies conjugated to fluorescent dyes. Briefly, after saturation with 2% human serum, mononuclear cells were incubated with the primary antibodies or appropriate isotype controls for 30 minutes at 4° C. in the dark. Cells were washed and fixed in 0.5% formaldehyde before the analysis on a LSRII or Fortessa cytometer (BD Biosciences). Flow cytometry data were analyzed with the Diva (BD Biosciences) and FlowJo (Tree Star, Inc) softwares.

Immunohistochemistry

For each paraffin-embedded lung tumor, two observers (one expert pathologist and one investigator trained to identify the pathological features of NSCLC) selected the tumor section containing a representative area of tumor with adjacent lung parenchyma, and the highest density of immune cells on hematoxylin and eosin-stained tissue section. Briefly, serial 5-μm tissue sections were deparaffinized, rehydrated, and pretreated in appropriate buffer for antigen retrieval. Then, the sections were incubated with 5% human serum for 30 minutes before adding the appropriate primary antibodies followed by secondary antibodies. Enzymatic activity was revealed, as described (Dieu-Nosjean. et al. J. Clin. Oncol 26, 4410-4417 (2008)). Images were acquired using a Nanozoomer (Hamamatsu) operated with NDPview software.

Method for Cell Quantification

DC-LAMP+ DCs were counted semi-quantitatively (score 0, 1, 2, 3, and 4 for none, very low, weak, intermediate, and high density of positive cells, respectively) in each intermediate-power field (IPF) in the tumoral areas of the entire tissue section and expressed as mean score per IPF, with SEMs calculated. The number of DC-Lamp$^+$ mature DCs was lower than the number of cells described above, allowing the inventors to realize a quantitative counting. Those stained cells were expressed as mean cells per IPF, with SEMs calculated.

CD8+ cells were enumerated in the tumor nests and the stroma of the whole tumor section with Calopix software, and expressed as an absolute number of positive cells/μm$^2$ of the areas of interest (Tribvn), with SEMs calculated. Both immunostaining and quantification were reviewed by at least two independent observers.

Statistical Analysis

The inventors used the Mann-Whitney test to compare the density of infiltrating immune cells in the different tumors. Correlations were evaluated by the Spearman test. OS curves were estimated by Kaplan-Meier method and differences between the groups of patients were calculated using the log-rank test. The start of follow-up for OS was the time of surgery. Together with mature DC and CD8+ T cells densities, the following available clinical parameters were tested: TNM stage 2009, T stage, N stage, smoking history, histologic type, adenocarcinoma subtype, emboli, and pleural invasion. With respect to immune cell densities, the "minimum P value" approach was used to determine the cutoff for the best separation of patients referring to their OS outcome (outcome-oriented approach). Because the P values obtained might be overestimated, OS log-rank P values were corrected using the formula proposed by Altman et al. or using 10-fold cross-validations. A P value less than 0.05 was considered statistically significant. Parameters identified at univariate analysis as possibly influencing outcome (P<0.05) were introduced in a multivariate Cox-proportional hazards regression model. All analyses were performed with Prism 5 (GraphPad), Statview (Abacus Systems) and the R. Correlation matrix was done using hierarchical clustering with Genesis software (Institute for Genomics and Bioinformatics, Gratz, Austria; Sturn et al., Bioinformatics, 2002).

1—High Density of Mature DC Predicts High Levels of $CD8^+$ T Cell Infiltration in Lung Tumors The inventors observed a close association between mature DC density with cytotoxic-effector function, the inventors further investigated the relationship between mature DC and $CD8^+$ T cell infiltration. Since $CD8^+$ T cells are expected to establish a contact with tumor cells to exert their cytolytic function, the inventors discriminated $CD8^+$ T cells present in the tumor nests and in the stroma in the following analysis.

In a retrospective series of 376 NSCLC patients (stages I to IV, UICC TNM classification 2009), the inventors quantified stromal $CD8^+$ T cells ($CD8_S$), tumor nest $CD8^+$ T cells ($CD8_T$) and mature DC-Lamp$^+$ DC. As previously observed in early-stage lung tumors, the inventors confirmed that mature DC home selectively in the T-cell rich areas of TLS adjacent to PNAd$^+$ vessels and B cell follicles in all stage lung tumors.

In accordance with the results above, the inventors observed a higher density of both $CD8_T$ and $CD8_S$ cells among DC-Lamp$^{Hi}$ versus DC-Lamp$^{Lo}$ tumors (mean=254 versus 138 $CD8_T$/mm$^2$, P=0.0003; mean=843 versus 553 $CD8_S$/mm$^2$ P<0.0001, respectively). Consequently, substratification of DC-Lamp$^{Hi}$ and DC-Lamp$^{Lo}$ patients according to $CD8_S$ and $CD8_T$ cell densities revealed that 84% of DC-Lamp$^{Hi}$ patients were $CD8^{Hi}$ in at least one region, and in particular 55% were high in both regions. These proportions were greatly reduced in DC-Lamp$^{Lo}$ patients with 61% of $CD8^{Hi}$ in at least one region, and only 33% in both regions. Interestingly, patients with $CD8_S^{Lo}$/$CD8_T^{Hi}$ tumors were rare in both DC-Lamp groups, in accordance with the trafficking of infiltrating T cells from the stroma to the tumor nests. The main differences between DC-Lamp$^{Hi}$ versus DC-Lamp$^{Lo}$ patients concerned the percentage of $CD8_S^{Hi}CD8_T^{Hi}$ and $CD8_S^{Lo}CD8_T^{Lo}$ patients while the percentages of mix groups ($CD8_S^{Hi}CD8_T^{Lo}$ and $CD8_S^{Lo}CD8_T^{Hi}$) were quite unchanged.

Altogether, these results demonstrate that a high density of mature DC is closely related to a strong $CD8^+$ T cell infiltration.

2—Mature DC Density is Associated with Early-Differentiated and Effector-Memory $CD8^+$ T Cell Infiltration in Human Lung Tumors The inventors performed large-scale flow cytometry analyses on 54 freshly resected human NSCLC to characterize the immune infiltrate according to the density of DC-Lamp$^+$ mature DC. The inventors observed a significant higher percentage of total $CD3^+$, $CD3^+CD4^+$ and $CD3^+CD8^+$ T cells, a non-significant trend for $CD19^+$ B cells and no difference for $CD3^-CD56^+$ NK cells among total mononuclear cells between patients with a high density of DC-Lamp$^+$ DC (DC-Lamp$^{Hi}$ patients) versus patients with a low density of DC-Lamp$^+$ DC (DC-Lamp$^{Lo}$ patients). DC-Lamp$^{Hi}$ tumors had a significantly greater amount of $CD62L^+$ $CD4^+$ and $CD62L^+CD8^+$ T cells than DC-Lamp$^{Lo}$ tumors, in accordance with the selective localization of $CD62L^+$ T cells inside the TLS. The inventors also observed a significant and concomitant increase of antigen-experienced $CD62L^-CD4^+$ and $CD62L^-CD8^+$ T cells, which represent the majority of TIL among total mononuclear cells, between DC-Lamp$^{Hi}$ versus DC-Lamp$^{Lo}$ tumors. As compared to DC-Lamp$^{Lo}$ tumors, DC-Lamp$^{Hi}$ tumors were more infiltrated by activated $CD38^+$ or $CD69^+$ $CD8^+$ T cells and by the four main subpopulations of effector-memory $CD8^+$ T cells ($CD45RA^-CCR7^-CD27^{+\ or\ -}CD28^{+\ or\ -}$).

Altogether, these results demonstrate that DC-Lamp$^{Hi}$ tumors have higher numbers of naïve and early-differentiated T cells associated with TLS, as well as a higher number of activated effector-memory non-TLS T cells, than DC-Lamp$^{Lo}$ tumors.

3—Density of TLS DC Allows the Identification of $CD8^{Hi}$ and $CD8^{Lo}$ Patients with High Risk of Death Since the inventors observed that high densities of $CD8^+$ T cells were detected in both groups of DC-Lamp$^{Hi}$ and DC-Lamp$^{Lo}$ patients, the inventors next evaluated the prognostic value of each variable alone and in combination.

The Kaplan-Meier curves indicate that the densities of mature DC (P=9.1×10$^{-05}$), $CD8_S$ cells (P=0.0019), and $CD8_T$ cells (P=0.0228) were correlated with longer overall survival (OS).

Since the presence of mature DC and $CD8^+$ cells in the tumors positively influence the outcome of lung cancer patients, the inventors stratified the patients into 4 groups according to the high or low density of each marker (DC-Lamp$^{Hi}$/$CD8^{Hi}$, DC-Lamp$^{Hi}$/$CD8^{Lo}$, DC-Lamp$^{Lo}$/$CD8^{Hi}$, and DC-Lamp$^{Lo}$/$CD8^{Lo}$). The inventors observed that the group of patients with DC-Lamp$^{Hi}$ tumors regardless of the density of $CD8_S$ cells had the lowest risk of death (P=3,4×10$^{-07}$, median OS were 92 months for DC-Lamp$^{Hi}$/$CD8_S^{Hi}$ patients and 100 months for DC-Lamp$^{Hi}$/$CD8_S^{Lo}$ patients), as was observed for DC-Lamp$^{Hi}$ patients. Interestingly, only the DC-Lamp$^{Hi}$ patients present an improved survival as compared to the whole cohort. In contrast, patients with a low density of both dendritic and $CD8_S$ cells were at highest risk of death (median OS was 22 months) as compared to each immune marker alone (mean OS DC-Lamp$^{Lo}$=36 months, mean OS $CD8_S^{Lo}$=40 months). Patients with DC-Lamp$^{Lo}$/$CD8_S^{Hi}$ tumors were at an intermediate risk of death (median OS=41 months). Same results were obtained when the analysis was performed on the combination of DC-Lamp with $CD8_T$ cells (data not shown). Additional analyses with 100 repetitions of two-fold cross-validations confirmed the high and significant prognostic value of DC-Lamp/$CD8_S$ score (cross-validated 99/100 tests, median P value=4.7×10$^{-04}$). Using Cox multivariate regression analyses, the pTNM stage and DC-Lamp/$CD8_S$ score were the only criteria significantly and independently associated with OS (HR=1.70 and 0.71, and P=2.83×10$^{-07}$ and 4.50×10$^{-07}$, respectively).

All together, these data demonstrate that DC-Lamp alone is a good marker for the identification of patients with a favorable outcome whereas the combination of CD8 with DC-Lamp allows the identification of patients with the highest risk of death. Finally, the DC-Lamp/$CD8_S$ score and pTNM stage constitute two independent and powerful prognostic factors.

Example 2

Patients

Paraffin-embedded lung tumor samples (n=372 tumors) were obtained from NSCLC patients (stages I to IV, UICC TNM classification 2009), who underwent a complete surgical resection of their lung tumors at Institut Mutualiste Montsouris or Hotel Dieu Hospital (Paris, France). Patients with an Eastern Cooperative Oncology Group performance status (Finkelstein et al., Am J Clin Oncol, 1988)≤1 were eligible. The classification of the tumor grade was made following the recommendation of the 7$^{th}$ edition of the TNM classification of malignant tumors published by the International Union Against Cancer and the American Joint Committee on Cancer (Sobin, Cancer, 2010). Patients operated between Jun. 15, 2001 and Dec. 31, 2004 were retrieved retrospectively. Patients who received neo-adjuvant chemotherapy or radiotherapy were ineligible. The observation time of the cohort was the interval between the diagnosis and the last contact (last follow-up or death of the patient). At the completion of the study, the minimal clinical follow-up was 90 months for the last patient included in the cohort. The data on long-term outcomes were obtained retrospectively by interrogation of municipality registers. A written informed consent was obtained from the patients prior to inclusion in the prospective study. The protocol was approved by the local ethic committee (n°: 2008-133 and 2012-0612) and by the Assistance Publique-Hopitaux de Paris (AP-HP), in application with the article L.1121-1 of French law.

1—Clinico-Pathologic Parameters of the Cohort

A total of 372 patients operated for a NSCLC (all stages) were enrolled in a retrospective study. The overall survival of the whole cohort is shown in FIG. 1A. As described in the literature, the pathologic T (pT) stage, N (pN) stage, TNM (pTNM) stage (7$^{th}$ edition, 2010), and tumor emboli were significantly correlated with the overall survival.

2—T Stage Better Predicts the Clinical Outcome of NSCLC Patients when Combined with the Density of Mature DC and CD8+ Cells Pathologic T stage is one of the gold standards in the clinic. As well established, pT was associated with longer survival of NSCLC patients (FIG. 2A, P<0.0001). The inventors then wanted to compare the prognostic value of the T stage according to the density of tumor-infiltrating DC-Lamp+ DC and CD8+ T cells.

Since the presence of mature DC and CD8+ T cells was previously demonstrated to be associated with favorable clinical outcome in NSCLC patients (see example 1), the inventors stratified the patients into 4 groups according to the high/low densities of DC-Lamp+ mature DC and CD8+ stromal T cells (DC CD8_Hi Hi, DC CD8_Hi Lo, DC CD8_Lo Hi, DC CD8_Lo Lo). As previously observed, the percentage of patients with "DC CD8_Hi Lo" tumors was very scarce that made the statistical analysis very difficult with this group, and interpretation very limited. FIG. 1B showed that the combination DC/CD8 is correlated with a favorable overall survival (P<0.0001). Then, the inventors studied the impact of the DC/CD8 score on patients stratified by pT stage.

Among pT1 stage, the Kaplan-Meier curves indicated that the density of the immune cells did not significantly correlate with survival (FIG. 2B). Patients with high density of at least one immune cell type (DC CD8_Hi Hi, DC CD8_Hi Lo or DC CD8_Lo Hi patients) had the same overall survival (OS) than pT1 patients (around 100 months). In contrast, patients with DC CD8_Lo Lo tumors had a worst prognosis as compared with those of pT1 patients (mean OS were 68 and 99 months, respectively). This tendency became even more significant at pT2 stage (mean OS=23 and 64 months for DC CD8_Lo Lo patients and pT2 patients, respectively).

Among pT2 stage, the combination DC/CD8 allowed the identification of groups of patients with long-term survival (mean OS for DC CD8_Hi Hi patients was 85 months) and short-term survival (mean OS for DC CD8_Lo Lo patients was 23 months) whereas patients with DC CD8_Lo Hi tumors had the same mean OS than pT2 patients (mean OS=69 and 64 months, respectively). Among pT3 stage, the high density of both DC and CD8+ T cells better predicted a favorable outcome (mean OS=69 months) than low density of DC regardless of the density of CD8+ T cells (mean OS=23 and 15 months for DC CD8_Lo Hi and DC CD8_Lo Lo patients, respectively) or pT3 stage patients (mean OS=24 months). The main difference between pT2 and pT3 stages in terms of survival, was the group of patients with DC CD8_Lo Hi tumors who switched from an intermediate to a high risk of death, respectively and had exactly the same outcome than groups of pT2 and pT3 patients.

All together, these data indicated that the combination of the density of both DC and CTL, and pT stage better predicts the overall survival of NSCLC patients than the gold standard pT stage alone.

3—Density of Both DC and CTL with the N Stage Better Predict the Clinical Outcome of NSCLC Patients than N Stage Alone The inventors next investigated the influence of DC/CD8 score on the prognostic value of the N stage (FIG. 3). N stage is known to be a prognostic marker for OS, as shown in FIG. 3A. Among patients without any detectable lymph node invasion, those with high density of infiltrating DC had a prolonged survival (mean OS were 99 and 111 months for patients with DC CD8_Hi Hi and DC CD8_Hi Lo tumors, respectively) whereas patients with DC CD8_Lo Lo had a very worse outcome (mean OS was 49 months), as compared to the reference which is patients with N0 stage (mean OS=73 months) (FIG. 3A-B). Patients with DC CD8_Lo Hi had a similar behavior as the reference N0 stage (mean OS=79 versus 73 months, respectively). For patients with lymph node involvement (FIG. 3A,C), the situation is even more striking There was a major difference for OS based on DC-Lamp stratification. As compared with the reference (mean OS=25 months for N+ patients), patients with high density of DC whatever the density of CD8+ T cells, had the highest rate and mean survival (10-year OS=45%, mean OS=64 months for DC CD8_Hi Hi patients). The same tendency was observed for DC CD8_Hi Lo patients but their number was too low to conclude). In contrast, patients with low density of DC had the worst rate and mean outcome (10-year OS=5%, mean OS=14 months). Again, the Kaplan-Meier curves for DC CD8_Lo Hi patients and N+ patients were exactly similar (FIG. 3A-C).

These results clearly demonstrated that the addition of DC and CD8 with the N stage (as the reference) allow a better discrimination of patients with high- versus low-risk of death, especially in the group of patients with lymph node invasion.

4—Combination of DC, CD8 and Emboli Better Predicts the Overall Survival than Emboli Alone Vascular and lymphatic invasion is an earliest sign of tumor cell spreading in the body. This criteria is also evaluated by clinicians as it is associated with poor survival, as shown in FIG. 4A. Thus, the inventors next studied the prognostic value of DC/CD8 score among NSCLC patients with or without emboli (FIG. 4). The combination DC/CD8 allowed a better identification of patients with favorable versus worst outcome (FIG. 4B-C) as compared with patients stratified by emboli alone (FIG. 4A). Among patients without any detectable emboli, the group of patients with low density of both immune cell types had a very poor OS (mean OS=54 months) whereas the 3 other groups had a slightly longer OS (mean OS were 92, 101 and 111 months for DC CD8_Hi Hi, DC CD8_Lo Hi, and DC CD8_Hi Lo patients, respectively), as compared with the group of emboli negative patients (mean OS=83 months). The immune criteria was much more predictive to survival for patients with emboli (FIG. 4C, P<0.0001). Patients with DC CD8_Hi Hi were at low risk of death (mean OS=84 months), patients with DC CD8_Lo Lo were at very high-risk for poor survival (mean OS=16 months) whereas patients with mix densities of immune cells had almost the same mean OS (mean OS were 46 and 32 months for DC CD8_Hi Lo and DC CD8_Lo Hi patients, respectively) than patients with emboli (mean OS=40 months).

These data show that the combination of DC, CD8 and emboli parameters allow a better stratification of NSCLC patients for survival.

5—Better Survival of NSCLC Patients Stratified by TNM Stage and DC/CD8 Score

Finally, the inventors tested the power of the prognostic value of the new pTNM classification (2010) with or without the DC/CD8 score (FIG. 5). As expected, TNM was a prognostic marker for OS (FIG. 5). As before, the prognostic impact of patients stratified by the immune score became more and more significant during disease progression. Since the early-stage of NSCLC, low densities of dendritic and CD8+ cells identified patients with the worst outcome (mean OS were 61 versus 99 months for DC CD8_Lo Lo patients and stage I patients, respectively; FIG. 5A-B) whereas the 3 other groups of DC/CD8 patients had the same mean OS as stage I patients. Among patients with the most advanced-stage of disease, those with high density of mature DC had a major benefit in terms of survival (mean OS=64 months) as compared to DC low groups of patients (mean OS were 10 and 13 months for DC CD8_Lo Hi and DC CD8_Lo Lo patients, respectively) or stage III patients (mean OS=18 months) (FIG. 5A,D). Again, whatever the stage of the disease, the DC CD8 Lo Hi patients always had the same behavior as those to the reference.

Altogether, the DC/CD8 score enhances the prognostic value of the TNM stage. Combining DC/CD8 score with the pTNM stage yields a more refined view of the prognosis of patients with a solid cancer with tumor-induced lymphoid structures such as NSCLC.

REFERENCES

Throughout this application, various references describe the state of the art to which this invention pertains. The disclosures of these references are hereby incorporated by reference into the present disclosure.

The invention claimed is:

1. A method for treating a patient suffering from a solid cancer containing tumor-induced lymphoid structures, wherein said method comprises the following steps:
    a) quantifying, in a tumor tissue sample from said patient, the cell density of cluster of differentiation 8-positive (CD8+) cells;
    b) quantifying, in a tumor-induced lymphoid structure from said patient, the cell density of dendritic cell-lysosomal associated membrane protein positive (DC-LAMP+) dendritic cells;
    c) comparing cell density values obtained at step a) and b) with predetermined reference values for each type of cells at each location; and
    d) providing the patient with an adjuvant therapy when each of the cell density of CD8+ cells and DC-LAMP+ dendritic cells are lower than said predetermined reference values.

2. The method of claim 1, wherein the patient is a patient with stage I cancer.

3. The method of claim 1, wherein the patient is a patient with stage II or III cancer.

4. The method of claim 1, wherein the tumor tissue sample is selected from the group consisting of (i) a global primary tumor sample as a whole, (ii) a tumor nest sample, and (iii) a stroma sample of the whole tumor section.

5. The method of claim 4, wherein the tumor tissue sample is in a stroma sample of the whole tumor section.

6. The method of claim 1, wherein the solid cancer is a lung cancer, a colorectal cancer or a breast cancer.

7. The method of claim 6, wherein the solid cancer is a lung cancer.

8. The method of claim 7, wherein the solid cancer is a non-small cell lung cancer.

9. A method for treating a patient suffering from a solid cancer containing tumor-induced lymphoid structures, wherein said method comprises the following steps:
    a) quantifying, in a tumor tissue sample from said patient, the cell density of CD8+ cells;
    b) quantifying, in a tumor-induced lymphoid structure from said patient, the cell density of DC-LAMP+ dendritic cells;
    c) comparing cell density values obtained at step a) and b) with predetermined reference values for each type of cells at each location; and
    d) providing the patient with a cytotoxic agent when each of the cell density of CD8+ cells and DC-LAMP+ dendritic cells are lower than said predetermined reference values.

10. The method of claim 9, wherein the patient is a patient with stage I cancer.

11. The method of claim 9, wherein the patient is a patient with stage II or III cancer.

12. The method of claim 9, wherein the tumor tissue sample is selected from the group consisting of (i) a global primary tumor sample as a whole, (ii) a tumor nest sample and (iii) a stroma sample of the whole tumor section.

13. The method of claim 12, wherein the tumor tissue sample is a stroma sample of the whole tumor section.

14. The method of claim 9, wherein the solid cancer is a lung cancer, a colorectal cancer or a breast cancer.

15. The method of claim 14, wherein the solid cancer is a lung cancer.

16. The method of claim 15, wherein the solid cancer is a non-small cell lung cancer.

* * * * *